US007504562B2

(12) United States Patent
Schut et al.

(10) Patent No.: US 7,504,562 B2
(45) Date of Patent: Mar. 17, 2009

(54) LETTUCE VARIETY

(75) Inventors: Johannes Wilhelmus Schut, BC Wouw (NL); Aad Ammerlaan, Aramon (FR); Cornelis Marinus Moor, An Monster (NL)

(73) Assignee: Rijk Zwaan Zaadteelt en Zaadhandel B.V., De Lier (NL)

( * ) Notice: Subject to any disclaimer, the term of this patent is extended or adjusted under 35 U.S.C. 154(b) by 0 days.

(21) Appl. No.: 11/451,974

(22) Filed: Jun. 13, 2006

(65) Prior Publication Data
US 2007/0006342 A1    Jan. 4, 2007

Related U.S. Application Data

(60) Provisional application No. 60/689,833, filed on Jun. 13, 2005.

(51) Int. Cl.
*A01H 1/00* (2006.01)
*A01H 5/00* (2006.01)
*A01H 5/10* (2006.01)

(52) U.S. Cl. .................. 800/305; 435/410; 800/260; 800/298

(58) Field of Classification Search .................. None
See application file for complete search history.

(56) References Cited

U.S. PATENT DOCUMENTS 5,973,232 A * 10/1999 Waycott et al. ............. 800/305
5,977,443 A    11/1999 Jansen
2005/0144672 A1   6/2005 Knerr

OTHER PUBLICATIONS

Pink et al 1992, Plant Pathology 41: 5-12.*
Palmumbo et al 2002, Vegetable Report, University of Arizona Collage of Agriculture and Life Sciences, "Population Growth of Lettuce Aphid, *Nasonova ribisnigris*, on Resistant Butter and Head Lettuce Cultivars".*

Michelmore et al 1987 Plant Cell Reports 6: 439-442.*
Van Ettekoven, K. et al. entitled "Identification and denomination of 'new' races of *Bremia lactucae*" In: Lebeda, A. and Kristkova, E (eds.), Eucarpia Leafy Vegetables, 1999, Palacky University, Olomouc, Czech Republic, pp. 171-175.
Bonnier, F.J.M. et al. entitled "New sources of major gene resistance in Lactuca to *Bremia lactucae*" Euphytica, 61(3), pp. 203-211, 1992.
Brown PR et al., entitled "The genetics of corky root resistance in lettuce" Phytopathology 78: 1145-1150, 1988.
Bruggen AHC Van et al., entitled "*Rhizomonas suberifaciens* gen. nov., sp. nov., the causal agent of corky root of lettuce" International Journal of Systematic Bacteriology. 40:2, 175-188, 1990.
Crute IR, entitled "From Breeding to cloning (and back again?): a case study with lettuce downy mildew" Annu. Rev. Phytopathol. 30: 485-506, 1992.
Pink Dac et al. entitled "Differentiation of pathotypes of lettuce mosaic virus" Plant Pathology 41:1, 5-12, 1992.
Upov entitled "Guidelines for the conduct of tests for distinctness, uniformity and stability; lettuce (*Lactuca sativa L.*)" International union for the protection of new varieties of plants. 35 pp., 2002.
Yabuuchi E, Kosako Y et al. entitled "Proposal of *Sphingomonas suberifaciens* (van Bruggen, Jochimsen and Brown 1990) comb. nov., *Sphingomonas natatoria* (Sly 1985) comb. nov., *Sphingomonas ursincola* (Yurkov et al. 1997) comb. nov., and emendation of the genus *Sphingomonas*" Microbial, Immunol 43: 339-349, 1999.

* cited by examiner

*Primary Examiner*—David H Kruse
(74) *Attorney, Agent, or Firm*—Frommer Lawrence & Haug LLP; Thomas J. Kowalski; Russell A. Garman

(57) ABSTRACT

The present invention relates to a *Lactuca sativa L.* var. *longifolia Lam* seed designated as 41-52 RZ, referred to as Nirvanus, which exhibits resistance against downy mildew (*Bremia lactucae Regel*), currant-lettuce aphid (*Nasonovia ribis-nigri*), corky root (*Sphingomonas suberifaciens*) and lettuce mosaic virus (LMV), the representative seed having been deposited with the National Collections of Industrial, Marine and Food Bacteria (NCIMB) in Bucksburn, Aberdeen AB21 9YA, Scotland, UK and assigned NCIMB Acession No. 41326. The present invention also relates to a *Lactuca sativa L.* var. *longifolia Lam* plant produced by growing the 41-52 RZ (Nirvanus) seed. The invention further relates to methods for producing the lettuce cultivar, represented by lettuce variety 41-52 RZ.

16 Claims, 1 Drawing Sheet

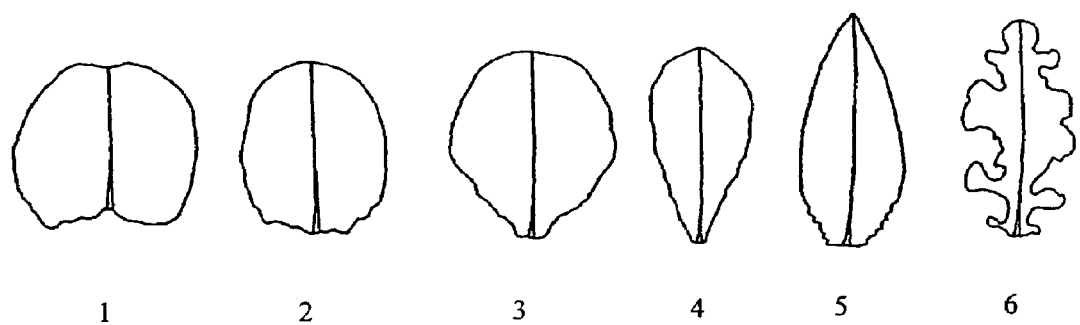
Fig. 1. Six different shapes of the fourth leaf from a 20-day old seedling grown under optimal conditions.

LETTUCE VARIETY

The present application claims the benefit of U.S. Provisional Application No. 60/689,833, filed Jun. 13, 2005, which is incorporated by reference in its entirety herein.

BACKGROUND OF THE INVENTION

1. Field of the Invention

The present invention relates to a new lettuce (*Lactuca sativa*) variety which exhibits resistance against downy mildew (*Bremia lactucae Regel*), currant-lettuce aphid (*Nasonovia ribis-nigri*), corky root (*Sphingomonas suberifaciens*), and lettuce mosaic virus (LMV).

2. Description of Related Art

All cultivated forms of lettuce belong to the highly polymorphic species, *Lactuca sativa*, which is grown for its edible head and leaves. As a crop, lettuces are grown commercially wherever environmental conditions permit the production of an economically viable yield.

*Lactuca sativa* is in the Cichoreae tribe of the Asteraceae (Compositae) family. Lettuce is related to chicory, sunflower, aster, dandelion, artichoke and chrysanthemum. *Sativa* is one of about 300 species in the genus *Lactuca*.

Lettuce cultivars are susceptible to a number of diseases such as downy mildew, currant-lettuce aphid, corky root and lettuce mosaic virus (LMV). These diseases result in millions of dollars of lost lettuce crop throughout the world every year.

Downy mildew (*Bremia lactucae Regel*) is highly destructive of lettuce grown at relatively low temperature and high humidity. Downy mildew is caused by a fungus, *Bremia lactucae Regel*, which can be one of the following strains: NL1, NL2, NL4, NL5, NL6, NL7, NL10, NL12, NL13, NL14, NL15, NL16, B1:17, B1:21 and B1:23 (Van Ettekoven, K. et al., "Identification and denomination of 'new' races of *Bremia lactucae*," In: Lebeda, A. and Kristkova, E (eds.), Eucarpia Leafy Vegetables, 1999, Palacky University, Olomouc, Czech Republic, pp. 171-175.)

Downy mildew causes pale, angular, yellow areas bounded by veins on the upper leaf surfaces. Sporulation occurs on the opposite surface of the leaves. The lesions eventually turn brown, and they may enlarge and coalesce. These symptoms typically occur first on the lower leaves of the lettuce, but under ideal conditions may move into the upper leaves of the head. When the fungus progresses to this degree, the head cannot be harvested. Less severe damage requires the removal of more leaves than usual, especially when the lettuce reaches its final destination.

Of the various species of aphids that feed on lettuce, the currant-lettuce aphid (*Nasonovia ribis-nigri*) is the most destructive species because it feeds both on the leaves of the lettuce as well as deep in the heart of the lettuce, making it difficult to control with conventional insecticides. The lettuce aphid feeds by sucking sap from the lettuce leaves. Although direct damage to the lettuce may be limited, its infestation has serious consequences because the presence of aphids makes lettuce unacceptable to consumers. Additionally, the lettuce aphid has a capacity to act as a vector for a number of viruses, such as gooseberry veinbanding virus, cauliflower mosaic virus, cucumber mosaic virus and lettuce mosaic virus.

Corky root (*Sphingomonas suberifaciens*) is a soilborne bacterium that is prevalent in most coastal lettuce growing areas. Corky root affects both leaf and head lettuce varieties. The disease typically is more severe when soil temperatures are warmer and in fields where lettuce is grown consecutively. High soil nitrate levels also increase disease severity. Early symptoms of corky root are yellow bands on tap and lateral roots of lettuce seedlings. The yellow areas gradually expand, taking on a greenish-brown color and developing cracks and rough areas on the surface of the root. As disease severity increases, the entire tap root may become brown, severely cracked, and nonfunctional; the feeder root system also may be reduced and damaged. At this point, roots are very brittle and easily break off when examined. Corky root also may cause internal discoloration of the root. When the root is severely diseased, aboveground symptoms consist of wilting during warm temperatures, stunting of plants, and general poor and uneven growth.

Lettuce mosaic virus (LMV) mainly infects lettuce seeds, which is the primary way that the virus is introduced to lettuce in the fields, but also can infect numerous crops and weeds, thereby creating reservoirs of the virus. LMV also can be vectored by aphids, which spread the virus within a lettuce field and introduce it into lettuce fields from infected weeds and crops outside the field.

Symptoms of lettuce mosaic virus vary greatly. Leaves of plants that are infected at a young stage are stunted, deformed, and (in some varieties) show a mosaic or mottling pattern. Such plants rarely grow to full size; head lettuce varieties infected early fail to form heads. Plants that are infected later in the growth cycle show a different set of symptoms. These plants may reach full size, but the older outer leaves turn yellow, twisted, and otherwise are deformed. On head lettuce, the wrapper leaves often will curve back away from the head and developing heads may be deformed. In some cases brown, necrotic flecks occur on the wrapper leaves.

There exists a need for an improved harvestable lettuce product which exhibits a combination of resistance against downy mildew (*Bremia lactucae Regel*), currant-lettuce aphid (*Nasonovia ribis-nigri*), corky root (*Sphingomonas suberifaciens*) and lettuce mosaic virus (LMV).

SUMMARY OF THE INVENTION

The present invention fulfills this need by providing a new variety of romaine, or cos, lettuce (*Lactuca sativa* L. var. *longifolia Lam*) plant, which exhibits a combination of resistance against downy mildew (*Bremia lactucae Regel*), currant-lettuce aphid (*Nasonovia ribis-nigri*), corky root (*Sphingomonas suberifaciens*) and lettuce mosaic virus (LMV). Seeds of lettuce cultivar 41-52 RZ have been deposited with the National Collections of Industrial, Marine and Food Bacteria (NCIMB) in Bucksburn, Aberdeen AB21 9YA, Scotland, UK and have been assigned NCIMB Acession No. 41326.

The present invention also provides parts of the plant of lettuce cultivar 41-52 RZ that are suitable for sexual reproduction, which include, without limitation, microspores, pollen, ovaries, ovules, embryo sacs or egg cells.

The present invention further provides parts of the plant of lettuce cultivar 41-52 RZ that are suitable for vegetative reproduction, which include, without limitation, cuttings, roots, stems, cells or protoplasts.

The present invention still further provides tissue culture of regenerable cells from lettuce cultivar 41-52 RZ in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems.

The present invention also provides a plant grown from the seeds, regenerated from the above-described plant parts, or regenerated from the above-described tissue culture having all of the morphological and physiological characteristics of lettuce cultivar 41-52 RZ.

The present invention further provides progeny of lettuce cultivar 41-52 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 41-52 RZ.

The present invention still further provides a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 41-52 RZ.

The present invention also provides a method of producing a lettuce cultivar having resistance to downy mildew (*Bremia lactucae Regal*), currant-lettuce aphid (*Nasonovia ribisnigri*), corky root (*Sphingomonas suberifaciens*), and lettuce mosaic virus (LMV), comprised of crossing a mother lettuce plant, such as, for example, and without limitation, a mother plant of the indoor butterhead lettuce variety, with a father lettuce plant, such as, for example, and without limitation, a father plant of a BC-5 product of a backcross program to introduce the CS-RL *Bremia* resistance factor.

BRIEF DESCRIPTION OF THE DRAWINGS

FIG. 1 is an illustration of six different shapes of the fourth leaf from a 20 day-old seedling grown under optimal conditions.

DETAILED DESCRIPTION OF THE INVENTION

The present provides a new variety of romaine, or cos, lettuce (*Lactuca sativa L.* var. *longifolia Lam*) plant, which exhibits a combination of resistance against downy mildew (*Bremia lactucae Regel*), currant-lettuce aphid (*Nasonovia ribis-nigri*), corky root (*Sphingomonas suberifaciens*) and lettuce mosaic virus (LMV). Seeds of lettuce cultivar 41-52 RZ have been deposited with the National Collections of Industrial, Marine and Food Bacteria (NCIMB) in Bucksburn, Aberdeen AB21 9YA, Scotland, UK and have been assigned NCIMB Acession No. 41326.

As used herein, "romaine" is the *Lactuca sativa L.* var. *longifolia Lam* plant; also known as "Cos." The plant develops in an upright open or upright compact growing habit with coarse textured leaves. The leaves are longer than they are wide—15 cupping together to form an elongated loose head. Leaf margins often are entire or undulated and rarely frilled. Outer leaves range in color from light green to dark green with a heavy midrib. Inner heart leaves are smaller and range from light yellow to light green in color.

As used herein, resistance against *Bremia lactucae Regal* is defined as the ability of a plant to resist infection by various strains of *Bremia lactuca* (NL1, NL2, NL4, NL5, NL6, NL7, NL10, NL12, NL13, NL14, NL15, NL16, B1:17, B1:21 and B1:23) via a hypersensitivity response (Crute, I. R., Annual Rev. Phytopathol., 30:485-506, 1992; incorporated herein by reference). Resistance is defined as the capacity of the plant to resist infection by each of the various strains of *Bremia lactucae Regal* in all stages between the seedling stage and the harvestable plant stage. Resistance typically is tested by two interchangeable methods, described by Bonnier, F. J. M. et al. (Euphytica, 61(3):203-211, 1992; incorporated herein by reference). One method involves inoculating 7-day old seedlings, and observing sporulation 10 to 14 days later. The other method involves inoculating leaf discs with a diameter of 18 mm obtained from a non-senescent, fully grown true leaf and observing sporulation 10 days later.

As used herein, resistance against *Nasonovia ribis-nigri* (Mosley), or currant-lettuce aphid, is defined as the plant characteristic which results in a non-feeding response of the aphid on the leaves of the plant in all stages between 5 true-leaf stage and harvestable plant stage (U.S. Pat. No. 5,977,443 to Jansen, J. P. A., "Aphid Resistance in Composites," p. 12, 1999; incorporated herein by reference). Resistance is tested by spreading at least ten aphids on a plant in a plant stage between 5 true leaves and harvestable stage, and observing the density of the aphid population on the plant as well as the growth reduction after 14 days in a greenhouse, with temperature settings of 23 degrees Celsius in daytime and 21 degrees Celsius at night. Daylength is kept at 18 hours by assimilation lights.

As used herein, resistance against *Sphingomonas suberifaciens*, also known as corky root or *Rhizomonas suberifaciens*, is defined as the ability of the plant to grow relatively normally in a corky root-infected soil (Yabuuchi, E. et al., Microbiol. Immunol., 43:339-349, 1997). As the resistance of the lettuce plant to the bacterium is incomplete, a susceptible and a resistant standard variety, for example "Parris Island" (susceptible) and "Tall Guzmaine" (resistant), should be used for comparison. Resistance is tested with a young plant test in a greenhouse using the CA1-strain of the bacterium, as described by Brown, P. R. et al. (Phytopathology, 78:1145-1150, 1988), incorporated herein by reference.

As used herein, resistance against lettuce mosaic virus (LMV) is defined as the ability of the plant to grow normally after LMV infection and to inhibit the virus transmission via seed. Resistance is tested by mechanical inoculation of young plants in a climate cell or a greenhouse, as described by Pink, D. A. C. et al. (Plant Pathology, 41(1):5-12, 1992), incorporated herein by reference. Inoculated resistant plants grow just as well as uninoculated plants and show no chlorosis or mosaic symptoms. The LMV isolate which is used for testing is Ls-1 (International Union for the Protection of New Varieties of Plants [UPOV]), Guidelines for the conduct of tests for distinctness, uniformity and stability; lettuce (*Lactuca sativa L.*), 2002, p. 35; incorporated herein by reference).

As used herein, an acceptable product for the lettuce processing industry and/or consumers is defined as the absence of tipburn and having a short core, dark green outer leaves and sufficient, yellow heart leaves.

In an embodiment of the present invention, there also is provided parts of the plant of lettuce cultivar 41-52 RZ that are suitable for sexual reproduction, which include, without limitation, microspores, pollen, ovaries, ovules, embryo sacs or egg cells.

In another embodiment, there is provided parts of the plant of lettuce cultivar 41-52 RZ that are suitable for vegetative reproduction, which include, without limitation, cuttings, roots, stems, cells or protoplasts.

In a further embodiment, there is provided tissue culture of regenerable cells from lettuce cultivar 41-52 RZ in which the cells or protoplasts of the tissue culture are derived from a tissue such as, for example and without limitation, leaves, pollen, embryos, cotyledon, hypocotyls, meristematic cells, roots, root tips, anthers, flowers, seeds or stems.

In still a further embodiment, there is provided a plant grown from the seeds, regenerated from the above-described plant parts, or regenerated from the above-described tissue culture having all of the morphological and physiological characteristics of lettuce cultivar 41-52 RZ.

In still another embodiment, there is provided progeny of lettuce cultivar 41-52 RZ produced by sexual or vegetative reproduction, grown from seeds, regenerated from the above-described plant parts, or regenerated from the above-described tissue culture of the lettuce cultivar or a progeny plant thereof, in which the regenerated plant has all of the morphological and physiological characteristics of lettuce cultivar 41-52 RZ. Progeny of the lettuce cultivar 41-52 RZ can be modified in one or more other characteristics, in which the modification is a result of, for example and without limitation, mutagenesis or transformation with a transgene.

In still a further embodiment, there is provided a method of producing a hybrid lettuce seed comprised of crossing a first parent lettuce plant with a second parent lettuce plant and harvesting the resultant hybrid lettuce seed, in which the first parent lettuce plant or the second parent lettuce plant is the lettuce cultivar 41-52 RZ.

In still another embodiment, there is provided a method of producing a lettuce cultivar having resistance to downy mildew (*Bremia lactucae Regal*), currant-lettuce aphid (*Nasonovia ribisnigri*), corky root (*Sphingomonas suberifaciens*), and lettuce mosaic virus (LMV), comprised of crossing a mother lettuce plant, such as for example and without limitation, a mother plant of the indoor butterhead lettuce variety, with a father lettuce plant, such as for example and without limitation, a father plant of a BC-5 product of a backcross program to introduce the CS-RL *Bremia* resistance factor.

In a preferred embodiment, the specific type of breeding method employed for developing a lettuce cultivar is pedigree selection, where both single plant selection and mass selection practices are employed. Pedigree selection, also known as the "Vilmorin system of selection," is described in Fehr, W., *Principles of Cultivar Development*, Volume I, MacMillan Publishing Co., which is hereby incorporated by reference.

In general, selection is first practiced among $F_2$-plants. In the next season, the most desirable $F_3$ lines are first identified, then desirable $F_3$ plants within each line are selected. The following season and in all subsequent generations of inbreeding, the most desirable families are identified first, then desirable lines within the selected families are chosen, and finally desirable plants within selected lines are harvested individually. A family refers to lines that were derived from plants selected from the same progeny from the preceding generation.

Using this pedigree method, two parents may be crossed using an emasculated female and a pollen donor (male) to produce $F_1$ offspring. Lettuce is an obligate self-pollination species, which means that pollen is shed before stigma emergence, assuring 100% self-fertilization. Therefore, in order to optimize crossing, a method of misting may be used to wash the pollen off prior to fertilization to assure crossing or hybridization.

Parental varieties are selected from commercial varieties that individually exhibit one or more desired phenotypes. Additionally, any breeding method involving selection of plants for the desired phenotype can be used in the method of the present invention.

The $F_1$ may be self-pollinated to produce a segregating $F_2$ generation. Individual plants may then be selected which represent the desired phenotype in each generation ($F_3$, $F_4$, $F_5$, etc.) until the traits are homozygous or fixed within a breeding population.

The present invention is more particularly described in the following non-limiting example, which is intended to be illustrative only, as numerous modifications and variations therein will be apparent to those skilled in the art.

EXAMPLE 1

Development and Characteristics of Lettuce Cultivar 41-52 RZ

The breeding history of lettuce cultivar 41-52 RZ started with a cross between the romaine lettuce "Candela" (Rijk Zwaan) and the iceberg lettuce "Fortunas" (Rijk Zwaan) for the purpose of introducing resistance against *Nasonovia ribis-nigri* (Nr-resistance) in the romaine type. An $F_1$-plant from this cross was used as a father in a backcross with a plant of "Candela." A resulting $F_1$-plant was grown in Hendrik-Ido-Ambacht, the Netherlands, to produce an $F_2$ seed. In 1998, the $F_2$ seed was sown in a spring trial in Aramon, France. In May, 1998, an $F_2$-plant was selected for being of the romaine type and being Nr-resistant. The $F_2$-plant produced $F_3$ seed, which was sown in a late summer trial in Aramon in 1998. In September, 1998, an $F_3$-plant was selected for being of the romaine type and being Nr-resistant. This plant was used as a mother in a cross with a father plant of the romaine lettuce "Bacio" (Enza Zaden). The purpose of using the variety "Bacio" was to introduce a dark green outer leaf color and resistance to *Bremia lactucae* (Bl-resistance) and LMV.

In 1999, a resulting $F_1$-plant was grown in Aramon to produce a white-colored $F_2$ seed, which was sown in a spring trial in Aramon in 2000. In May, 2000, an $F_2$-plant was selected for being a dark green romaine type and being Bl- and Nr-resistant. This plant was used as a father in a cross with a mother plant of the romaine lettuce "King Henry" (Progeny Advanced Genetics; PVP 9600323). The purpose of using the black-seeded variety "King Henry" was to introduce resistance against *Sphingomonas suberifaciens* (Ss-resistance) and LMV.

In 2000, a resulting $F_1$-plant was grown in Aramon to produce an $F_2$ seed designated 01.49923. This seed was sown in a late summer trial in Fijnaart, the Netherlands, in 2001. In September, 2001, an $F_2$-plant was selected for being a dark green romaine type and being Bl-, Ss-, LMV- and Nr-resistant. The $F_2$-plant produced $F_3$ seed, designated 02.50570, which was sown in a spring trial in Aramon in 2002. In May, 2002, it was observed in this trial that the $F_3$ line produced a harvestable product, which was acceptable for the lettuce processing industry and/or for consumers. At the same time, an $F_3$-plant was selected from the trial for being a dark green romaine type and being Bl-, Ss-, LMV- and Nr-resistant. The $F_3$-plant produced $F_4$ seed, designated 03.52748, which was sown in an autumn trial in Aramon in 2002. In October, 2002, it was observed in this trial that the $F_4$ line produced a harvested product, which was acceptable for the lettuce processing industry and/or for consumers. At the same time, an $F_4$-plant was selected from the trial for being a dark green romaine type and being Bl-, Ss-, LMV- and Nr-resistant. The $F_4$-plant produced $F_5$ seed, designated 03.54400, which was sown in an early summer trial in Fijnaart in 2003. In June, 2003, it was observed in this trial that the $F_5$ line produced a harvestable product, which was acceptable for the lettuce processing industry and/or for consumers. At the same time, an $F_5$-plant was selected from the trial for being a dark green romaine type and being Bl-, Ss-, LMV- and Nr-resistant.

The $F_5$-plant produced $F_6$ seed, designated 04.51631, which was uniform for type, field performance, bolting and sensitivity for tipburn (all based on several trials in 2004). It also was uniformly resistant against downy mildew (*Bremia lactucae Regel*), currant-lettuce aphid (*Nasonovia ribis-nigri*), corky root (*Sphingomonas suberifaciens*) and lettuce mosaic virus (LMV) in tests performed in 2003 and 2004. In October, 2003, the $F_6$ seed was used to sow a multiplication in Daylesford, Australia. The plants showed phenotypical uniformity during seed production and seed was harvested for further trials in 2004.

In several trials in 2004, the multiplied seed, designated by the introduction number 41-52 RZ and referred to as "Nirvanus," showed a harvested product which was acceptable for the lettuce processing industry and/or for consumers.

The distinctive resistance characteristics of the "Nirvanus" seeds and plants of the present invention provide a significant advantage for growers trying to grow romaine lettuce at a low cost price. The combination of resistances prevents the "Nirvanus" plant from getting attacked by the four main pathogens of lettuce: downy mildew, corky root, currant-lettuce aphid and lettuce mosaic virus. This has the advantage of reducing the number of insecticide and fungicide sprays as well as the need for soil treatment or crop rotation to avoid corky root problems. The combined resistances of the "Nirvanus" seeds and plants of the present invention also provide the grower with less harvest losses due to these pathogens, which results in a higher yield per unit area. Additionally, it alleviates consumers' concerns about pesticide residues on their lettuce due to this reduction or absence of pesticide applications on the lettuce crops.

In the Tables that follow, the traits and characteristics of the *Lactuca sativa L.* var. *longifolia Lam* romaine lettuce plant referred to as "Nirvanus" and having the designation 41-52 RZ, are given compared to the most similar variety, referred to as "King Henry," and a standard regional check variety, referred to as "Parris Island."

In Table 1, the seed color, cotyledon shape and characteristics of the fourth leaf of "Nirvanus" is compared with "King Henry" and "Parris Island." The "Leaf Length/Width Index" is found by dividing the length by the width and multiplying by 10.

TABLE 1

| CHARACTER | "NIRVANUS" | "KING HENRY" | "PARRIS ISLAND" |
| --- | --- | --- | --- |
| Plant Type | Romaine or Cos | Romaine or Cos | Romaine or Cos |
| Seed Color | Black (Grey Brown) | Black (Grey Brown) | White (Silver Gray) |
| Cotyledon Shape | Spatulate | Intermediate | Intermediate |
| Cotyledon Shape of Fourth Leaf | No. 4 on FIG. 1 | No. 4 on FIG. 1 | No. 4 on FIG. 1 |
| Cotyledon Rolling of Fourth Leaf Stage | Absent | Absent | Absent |
| Cotyledon Cupping of Fourth Leaf Stage | Uncupped | Slight | Uncupped |
| Fourth Leaf Length/Width Index | 23 | 23 | 23 |
| Fourth Leaf Apical Margin | Entire | Entire | Entire |
| Fourth Leaf Basal Margin | Moderately Dentate | Moderately Dentate | Moderately Dentate |
| Undulation | Flat | Flat | Flat |

In Table 2, the mature leaf and head characteristics of "Nirvanus" is compared with "King Henry" and "Parris Island."

TABLE 2

| CHARACTER | "NIRVANUS" | "KING HENRY" | "PARRIS ISLAND" |
| --- | --- | --- | --- |
| Maturity (Earliness of Harvest-Mature Head Formation | 65 days | 69 days | 71 days |
| (Spring season) | | | |
| Green Color | Medium Green | Medium Green | Medium Green |
| Anthocyanin Distribution | Absent | Absent | Absent |
| Margin Incision Depth | Absent/Shallow | Absent/Shallow | Absent/Shallow |
| Margin Indentation | Entire | Entire | Entire |
| Undulations of the Apical Margin | Absent/Slight | Absent/Slight | Absent/Slight |
| Leaf Size | Large | Large | Large |
| Leaf Glossiness | Moderate | Moderate | Dull |
| Leaf Blistering | Moderate | Strong | Absent/Slight |
| Leaf Thickness | Thick | Thick | Thick |
| Trichomes | Absent (Smooth) | Absent (Smooth) | Present (Spiny) |
| Spread of Frame Leaves | 39 cm | 41 cm | 43 cm |
| Head Diameter | 25 cm | 24 cm | 29 cm |
| Head Shape | Elongate | Elongate | Elongate |
| Head Size | Large | Large | Large |
| Head Weight | 874 g | 929 g | 1368 g |
| Head Firmness | Firm | Firm | Firm |
| Butt Shape | Rounded | Rounded | Rounded |
| Midrib | Prominently Raised | Moderately Raised | Elongate |

In Table 3, the characteristics of the core and the bolter plant of "Nirvanus" is compared with "King Henry" and "Parris Island."

TABLE 3

| CHARACTER | "NIRVANUS" | "KING HENRY" | "PARRIS ISLAND" |
| --- | --- | --- | --- |
| Core Diameter at Base of Head | 41 mm | 40 mm | 51 mm |
| Ratio of Head Diameter/Core Diameter | 6.1 | 6.0 | 5.7 |
| Core Height from Base of Head to | 68 mm | 67 mm | 74 mm |

TABLE 3-continued

| CHARACTER | "NIRVANUS" | "KING HENRY" | "PARRIS ISLAND" |
|---|---|---|---|
| Apex | | | |
| Number of Days from first water date to seed stalk emergence | 101 | 93 | 93 |
| Bolting Class | Very Slow | Very Slow | Very Slow |
| Height of Mature Seed Stalk | 120 cm | 115 cm | 130 cm |
| Spread of Bolter Plant | 30 cm | 20 cm | 30 cm |
| Bolter Leaves | Straight | Straight | Straight |
| Margin | Entire | Entire | Entire |
| Color | Dark Green | Dark Green | Dark Green |
| Terminal Inflorescence | Absent | Present | Absent |
| Lateral Shoots | Present | Absent | Present |
| Basal Side Shoots | Present | Absent | Absent |

While the invention has been particularly shown and described with reference to preferred embodiments thereof, it will be understood by those skilled in the art that various alterations in form and detail may be made therein without departing from the spirit and scope of the invention.

The invention claimed is:

1. A lettuce plant designated 41-52 RZ, referred to as Nirvanus, representative seed of which having been deposited under NCIMB Accession No. 41326, wherein said plant has resistance to downy mildew (*Bremia lactucae Regal*), currant-lettuce aphid (*Nasonovia ribisnigri*), corky root (*Sphingomonas suberifaciens*), and lettuce mosaic virus (LMV).

2. A seed of the plant of claim 1.

3. A part of the plant of claim 1, wherein said part of the plant is suitable for sexual reproduction.

4. The part of the plant as claimed in claim 3, said part selected from the group consisting of microspores, pollen, ovaries, ovules, embryo sacs and egg cells.

5. The part of the plant of claim 1, wherein said part of the plant is suitable for vegetative reproduction.

6. The part as claimed in claim 5, said part selected from the group consisting of cuttings, roots, stems, cells and protoplasts.

7. A tissue culture of regenerable cells or protoplasts from the lettuce plant of claim 1.

8. The tissue culture as claimed in claim 7, wherein said cells or protoplasts of the tissue culture which are produced from a tissue selected from the group consisting of leaves, pollen, embryos, cotyledon, hypocotyls, meristematic cells, roots, root tips, anthers, flowers, seeds and stems.

9. A plant that has all of the morphological and physiological characteristics of lettuce cultivar 41-52 RZ, representative seed of which having been deposited under NCIMB Accession No. 41326, said plant grown from seeds as claimed in claim 2.

10. A plant that has all of the morphological and physiological characteristics of lettuce cultivar 41-52 RZ, representative seed of which having been deposited under NCIMB Accession No. 41326, said plant regenerated from parts of the plant as claimed in claim 3.

11. A plant that has all of the morphological and physiological characteristics of lettuce cultivar 41-52 RZ, representative seed of which having been deposited under NCIMB Accession No. 41326, said plant regenerated from a tissue culture as claimed in claim 7.

12. A progeny of a lettuce plant of claim 1, wherein said progeny is produced by sexual or vegetative reproduction of said lettuce plant or a progeny plant thereof, and wherein the progeny has all of the morphological and physiological characteristics of lettuce cultivar 41-52 RZ, representative seed of which having been deposited under NCIMB Accession No. 41326.

13. A progeny of a lettuce plant of claim 9, wherein said progeny is produced by sexual or vegetative reproduction of said lettuce plant or a progeny plant thereof, and wherein the progeny has all of the morphological and physiological characteristics of lettuce cultivar 41-52 RZ, representative seed of which having been deposited under NCIMB Accession No. 41326.

14. A progeny of a lettuce plant of claim 10, wherein said progeny is produced by sexual or vegetative reproduction of said lettuce plant or a progeny plant thereof, and wherein the progeny has all of the morphological and physiological characteristics of lettuce cultivar 41-52 RZ, representative seed of which having been deposited under NCIMB Accession No. 41326.

15. A progeny of a lettuce plant of claim 11, wherein said progeny is produced by sexual or vegetative reproduction of said lettuce plant or a progeny plant thereof, and wherein the progeny has all of the morphological and physiological characteristics of lettuce cultivar 41-52 RZ, representative seed of which having been deposited under NCIMB Accession No. 41326.

16. A method of producing a hybrid lettuce seed comprising crossing a first parent lettuce plant with a second parent lettuce plant and harvesting the resultant hybrid lettuce seed, wherein said first parent lettuce plant or said second parent lettuce plant is the lettuce plant of claim 1.

* * * * *

UNITED STATES PATENT AND TRADEMARK OFFICE
Certificate

Patent No. 7,504,562 B2                                Patented: March 17, 2009

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Aad Ammerlaan, Aramon (FR).

Signed and Sealed this Sixth Day of December 2011.

ANNE GRUNBERG
*Supervisory Patent Examiner*
Art Unit 1638
Technology Center 1600